United States Patent
Clevett

(10) Patent No.: US 11,864,774 B2
(45) Date of Patent: Jan. 9, 2024

(54) ADAPTER ASSEMBLY FOR SURGICAL CUTTING TOOL

(71) Applicant: Arthrex, Inc., Naples, FL (US)

(72) Inventor: James Tyler Clevett, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 145 days.

(21) Appl. No.: 17/470,503

(22) Filed: Sep. 9, 2021

(65) Prior Publication Data

US 2023/0070919 A1    Mar. 9, 2023

(51) Int. Cl.
*A61B 17/15* (2006.01)
*A61B 17/14* (2006.01)
*A61B 17/00* (2006.01)

(52) U.S. Cl.
CPC ............ *A61B 17/15* (2013.01); *A61B 17/149* (2016.11); *A61B 2017/00486* (2013.01)

(58) Field of Classification Search
CPC ........ A61B 2017/00486; A61B 17/149; A61B 17/15; B23D 61/18
See application file for complete search history.

(56) References Cited

U.S. PATENT DOCUMENTS

| | | | |
|---|---|---|---|
| 7,846,165 B2 | 12/2010 | Aram et al. | |
| 8,499,674 B2 * | 8/2013 | Holba | B27B 19/006 83/746 |
| 8,585,704 B2 | 11/2013 | Schmitz et al. | |
| 8,740,906 B2 | 6/2014 | Haines | |
| 2008/0115367 A1 | 5/2008 | Glynn | |

FOREIGN PATENT DOCUMENTS

| | | |
|---|---|---|
| JP | 5406365 B2 | 2/2014 |
| JP | 5607100 B2 | 10/2014 |
| WO | 2013077862 A1 | 5/2013 |
| WO | 2020023664 A1 | 1/2020 |

* cited by examiner

*Primary Examiner* — Larry E Waggle, Jr.
(74) *Attorney, Agent, or Firm* — Price Heneveld LLP

(57) ABSTRACT

An adapter apparatus for a cable saw or similar cutting implement includes a hub adapter that may detachably engage a mounting hub of a power tool. A pair of lateral arms extend outward on opposing sides of the hub adapter to a connection interface of the cable saw. The connection interface engages opposing wire ends of the cable saw and provides for a cutting operation in response to an oscillating motion of the power tool.

21 Claims, 5 Drawing Sheets

ADAPTER ASSEMBLY FOR SURGICAL CUTTING TOOL

BACKGROUND

The present disclosure generally relates to an adapter for a surgical cutting tool and, more particularly, to an adapter for a wire or cable saw that mounts a cutting wire to an oscillating power tool. Power tools may be implemented in a variety of surgical applications to selectively remove tissue or provide a variety of beneficial utilities for medical procedures. In order to suit the specific needs of each type of operation, some power tools may incorporate interchangeable head assemblies or cutting blades that may be swapped and exchanged to apply the tool for a variety of applications. The adapter apparatus of the disclosure may provide for the utilization of a cable or wire saw with various power tools.

SUMMARY

In various embodiments, the disclosure provides an adapter apparatus for a cable saw or similar cutting tool that implements a cutting wire. The adapter apparatus may be implemented with an oscillating power tool that may alternately be applied in connection with an oscillating saw blade (e.g., a sagittal saw blade). The adapter apparatus may be implemented in a variety of forms and generally may provide for the selective attachment of a cable saw with a mounting hub of the oscillating power tool. In general, the cable saw may correspond to various cutting tools that incorporate a flexible cutting line, cord, or wire that is connected on opposing sides to the adapter apparatus. Accordingly, the adapter apparatus may apply alternating tensile force to the opposing wire ends of the cutting wire to induce rapid, alternating translational movement along the length of the cutting wire. The rapid alternating movement may generate friction to effectively cut and remove material where the wire engages the bone or tissue.

In order to provide a connection of the cable saw, the adapter apparatus may include a hub adapter that detachably engages the mounting hub of the power tool. In this configuration, the cable saw adapter may be swapped or exchanged for various cutting blades or implements. In general, the adapter apparatus may include lateral arms that extend outward on opposing sides of the hub adapter. The lateral extension of the lateral arms on either side of the hub adapter may provide for a connection interface separated over a span between opposing ends of the cutting wire of the cable saw. In this way, the adapter apparatus may convert the angular oscillations of a drive shaft of the oscillating power tool to generate a translational seesaw motion in lateral end portions of the arms of the adapter. In operation, the translational motion of the arms alternately applies tension to the opposing ends of the cutting wire of the cable saw, which draws the cutting wire back and forth to generate friction over a cutting length to cut through bone, tissue, or various materials.

In various implementations, the adapter apparatus may include one or more of the following features:
- the mounting hub defines a rotational axis of a drive shaft of an oscillating power tool and the rotational axis extends centrally through the hub adapter in an assembled configuration;
- the hub adapter comprises a plurality of openings forming a mounting pattern that engages a mounting assembly of the mounting hub;
- the lateral arms form lateral wings mirrored across a medial axis extending from the proximal end portion of the hub adapter through the distal end portion of the extension portion;
- the mounting hub extends from a proximal end portion to a distal end portion forming an extension portion;
- each of the lateral arms extend from the extension portion to lateral end portions and the connection interface is laterally offset over a span;
- the lateral arms comprise a first arm and a second arm opposite the first arm and the extension portion extends to an extension distance along a medial axis of the adapter apparatus from the hub adapter; and
- the first arm and the second arm extend laterally outward from the distal end portion of the extension portion and wrap partially around a perimeter of the hub adapter from the extension portion to the span.

In some implementations, the adapter apparatus for the cable saw may include a hub adapter that detachably engages a mounting hub of a power tool. An extension portion is in connection with the hub adapter and forms a proximal end portion of the adapter apparatus. The extension portion extends from the hub adapter outward toward a distal end portion that is in connection with a first lateral arm and a second lateral arm. The first lateral arm and the second lateral arm extend laterally outward from the extension portion on opposing sides to a first lateral end portion and a second lateral end portion, respectively. A connection interface includes a first connecting feature and a second connecting feature that are laterally offset over a span. The first connecting feature is formed in the first lateral end portion of the first lateral arm and the second connecting feature is formed in the second lateral end portion of the second lateral arm. The connection interface connects to wire ends of a cutting wire of the cable saw.

In various implementations, the adapter apparatus may include one or more of the following features:
- the first connecting feature and the second connecting feature of the connection interface are laterally offset from or laterally aligned with a rotational axis of the hub adapter;
- the mounting hub is in connection with a driving head of the cutting tool, and the cutting tool generates an oscillating motion defining an arc-shaped stroke length that rotates the adapter apparatus about the rotational axis;
- the extension portion forms a medial distal extent of the adapter apparatus extending outward along the medial axis from the hub adapter;
- a support guide extending around a cable of the cable saw from the connection interface to a distal guide extent proximate to a cutting segment of the cable saw;
- the support guide extends from the connection interface along a guide plane perpendicular to the rotational axis along which an oscillation of the cable saw adjusts a circumferential position of the cable;
- the oscillating motion of the arc-shaped stroke adjusts a circumferential position of the cutting segment along the guide plane;
- a lateral support extending from the distal end portion along an oscillation path of the first lateral arm and the second lateral arm; and
- the lateral support forms a first thickness and the hub adapter forms a second thickness, wherein the second thickness is less than the first thickness.

In some implementations, an adapter apparatus for a cable saw is disclosed that comprises a hub adapter that detachably engages a mounting hub of a power tool. The hub adapter extends from a proximal end portion to a distal end portion forming an extension portion. The hub adapter extends outward over an extension distance along a medial axis from the hub adapter to the distal end portion. A first lateral arm and a second lateral arm extend outward on opposing sides of the hub adapter from the extension portion to lateral end portions. A connection interface of the cable saw is in connection with the lateral end portions of each of the first lateral arm and the second lateral arm. In this configuration, the connection interface is laterally offset over a span between the end portions of the first lateral arm and the second lateral arm.

In various implementations, the adapter apparatus may include one or more of the following features:

- the connection interface comprises a first connection feature disposed on a first lateral end portion of the first arm and a second connection feature disposed on a second lateral end portion of the second arm;
- at least one of the first connection feature and the second connection feature comprise a receiving aperture formed in the first lateral end portion or the second lateral end portion;
- the receiving aperture forms an interior wall defining an inner diameter, and a groove is formed in the interior wall of the receiving aperture and a retaining spring is disposed in the groove;
- the cable saw comprises at least one mounting pin in connection with a wire end of a cutting wire, wherein the mounting pin engages the receiving aperture and is free to rotate within the receiving aperture;
- the retaining spring is a toroidal retaining spring that conforms to the first groove in the receiving aperture;
- each of the first connection feature and the second connection feature comprise the receiving aperture, and the cable saw comprises mounting pins in connection with wire ends of a cutting wire, wherein the mounting pins engage the receiving apertures; and
- the mounting pins comprise a second annular groove that aligns with the retaining spring and the first annular groove retaining the mounting pins in the receiving apertures in an assembled configuration.

These and other features, objects and advantages will become apparent upon reading the following description thereof together with reference to the accompanying drawings.

DETAILED DESCRIPTION

The disclosure generally provides an adapter apparatus for a cable saw that may be implemented to modify an oscillating cutting tool to provide cable saw or wire cutting functionality. The power tool may correspond to a surgical power tool that includes a mounting hub configured to connect to a variety of cutting utilities. The power tool may utilize a variety of interchangeable drive heads to complete various operations. For example, the drive heads may provide for various operations, which may include drilling, reaming, sawing, wire/pin driving, burring etc. In some cases, the power tool may provide for the generation of a rapid, oscillating motion that may be applied in connection with a saw blade or cutting blade (e.g., a sagittal saw blade). The adapter apparatus may provide for the utilization of a cable saw or wire cutting apparatus that may be utilized with a sawing or oscillating drive head of a power tool interchangeably with other oscillating attachments or cutting tools.

Figure 1:
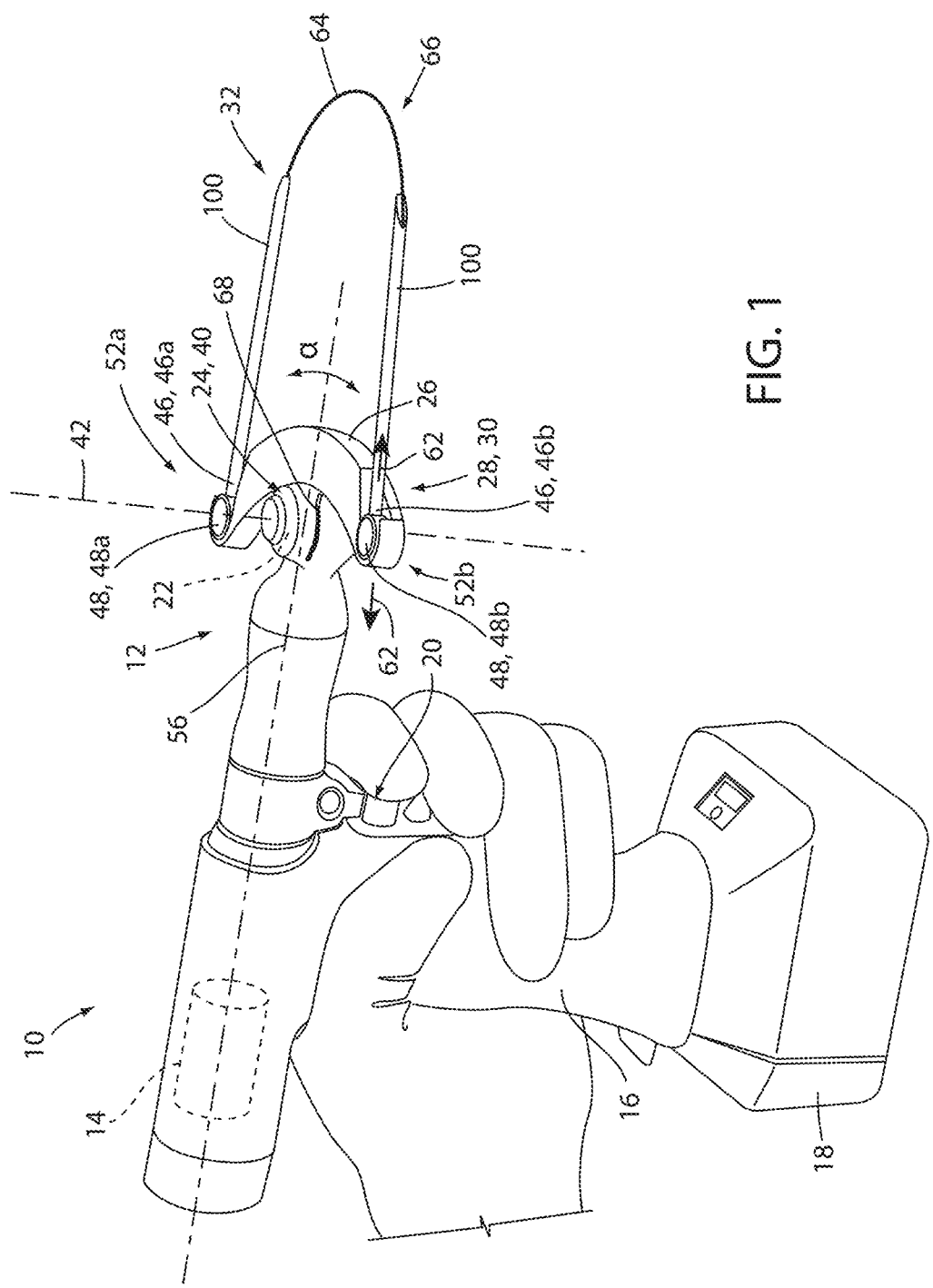
FIG. 1 is a projected view of a surgical cutting tool demonstrating a cable saw adapter apparatus.

Referring to FIG. 1, an exemplary implementation of a power tool 10 with an oscillating drive head 12 is shown. The power tool 10 may include a motor 14 disclosed in a housing 16 that forms a grip or handle, which is further in connection with a power supply 18. The operation of the power tool 10 may be activated in response to depressing a trigger assembly 20, which may supply power from the power supply 18 to the motor 14, such that the oscillating drive head 12 is activated. The activation of the oscillating drive head 12 may cause a drive shaft 22 disposed in a mounting hub 24 to rapidly oscillate in an alternating clockwise and counterclockwise motion over an angular range α. In various implementations, the angular range may be limited (e.g., approximately 1°-8°, 3°-5°, etc.), such that the alternating clockwise and counterclockwise movement results in a translational oscillatory motion at a distal extent 26 of a working attachment 28 of the power tool 10.

As demonstrated in FIGS. 1-5, an exemplary embodiment of the working attachment 28 may correspond to an adapter apparatus 30 for a cable saw 32. In various implementations, the adapter apparatus 30 may provide for the connection of the cable saw 32 to the mounting hub 24 of the power tool 10 via a hub adapter 34. The hub adapter 34 may correspond to a half-round or circular mounting interface that may include a mounting pattern 36 comprising a plurality of mounting apertures 38. The hub adapter 34 may be affixed to the mounting hub 24 via a clamping mechanism 40 of the power tool 10. When connected to the mounting hub 24, a rotational axis 42 of the drive shaft 22 may be aligned with a central axis 44 of the hub adapter 34. In this way, the angular rotation of the drive shaft 22 of the power tool 10 may cause the adapter apparatus 30 to rapidly oscillate over the angular range α.

The adapter apparatus 30 may connect to opposing wire ends 46 of the cable saw 32 via a connection interface 48. The connection interface 48 may comprise a first connecting feature 48a and a second connecting feature 48b that connect to a first wire end 46a and a second wire end 46b, respectively. Though discussed in reference to specific exemplary connecting features 48a, 48b, the wire ends 46a, 46b may be permanently affixed (e.g. welded, soldered, crimped, etc.), coupled, or generally retained in connection with the opposing lateral arms 50 via the connection interface 48. The connecting features 48a, 48b may each be disposed in or connected to lateral arms 50 that connect to opposing sides (e.g., a first side 52a, a second side 52b) of the hub adapter 34. More specifically, in some implementations, the hub adapter 34 may form a proximal end portion 54a that extends to a distal end portion 54b along a medial axis 56 of the hub adapter 34. The distal end portion 54b may correspond to an extension portion 58 that extends outward along the medial axis 56 away from the mounting hub 24 in an assembled configuration with the oscillating drive head 12. In various implementations, the lateral arms 50 may include a first lateral arm 50a and a second lateral arm 50b that extend perpendicularly or laterally outward from the extension portion 58 of the hub adapter 34 to a first lateral end portion 60a and a second lateral end portion 60b, respectively. The first connecting feature 48a may be connected to or disposed in the first lateral end portion 60a and the second connecting feature 48b may similarly be connected to or disposed in the second lateral end portion 60b. In this configuration, a span S may extend between the connecting features 48a, 48b that form the connection interface 48 of the hub adapter 34.

In operation, a lateral extension of each of the lateral arms 50 over the span S may provide for the angular range α of the oscillation generated by the oscillating drive head 12 of the power tool 10 to be converted into a translational seesaw motion induced into each of the lateral end portions 60 and the connecting features 48a, 48b on the opposing sides 52 of the hub adapter 34. In connection with the opposing wire ends 46 of the cable saw 32, the oscillating translational seesaw motion may cause alternating tension, denoted by numeral 62, to be applied to the opposing wire ends 46 via the connecting features 48a, 48b. Accordingly, the rapid alternating angular oscillations of the drive head 12 over the angular range α may result in the alternating seesaw motion induced in the lateral end portions 60 of the lateral arms 50 to generate the alternating tension 62. When applied to the opposing wire ends 46, the alternating tension 62 may result in a rapid back-and-forth motion of a cutting wire 64 of the cable saw 32, which may be utilized to cut material bound within a cutting loop 66 formed by the cable saw 32. In this way, the adapter apparatus 30 may provide for the application of the cable saw 32 as a working attachment 28 for connection with the oscillating drive head 12 of the power tool 10.

Figure 2:
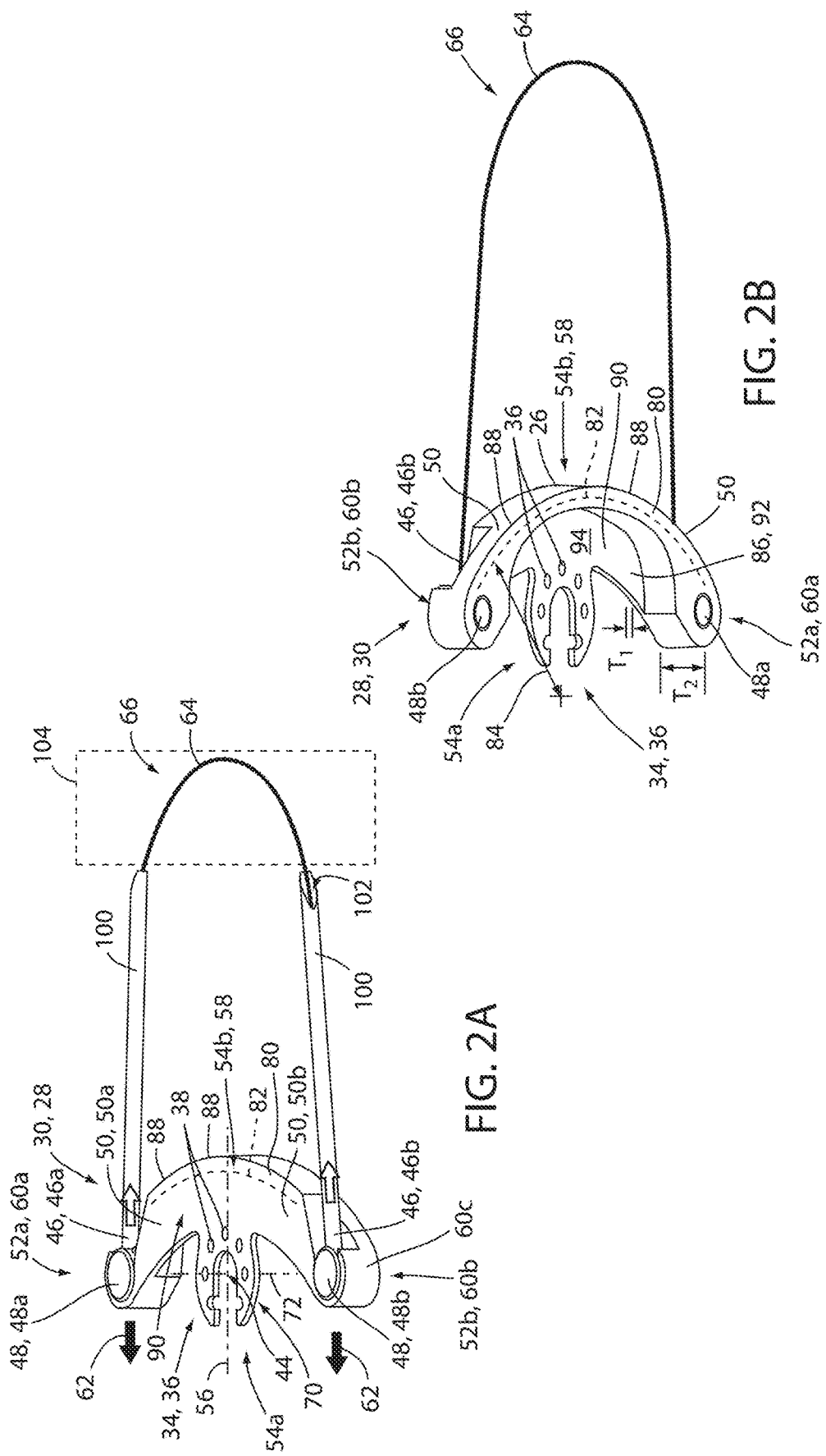
FIG. 2A is a top projected view of an adapter apparatus for a cable saw.
FIG. 2B is a bottom projected view of an adapter apparatus for a cable saw.
Figure 3:
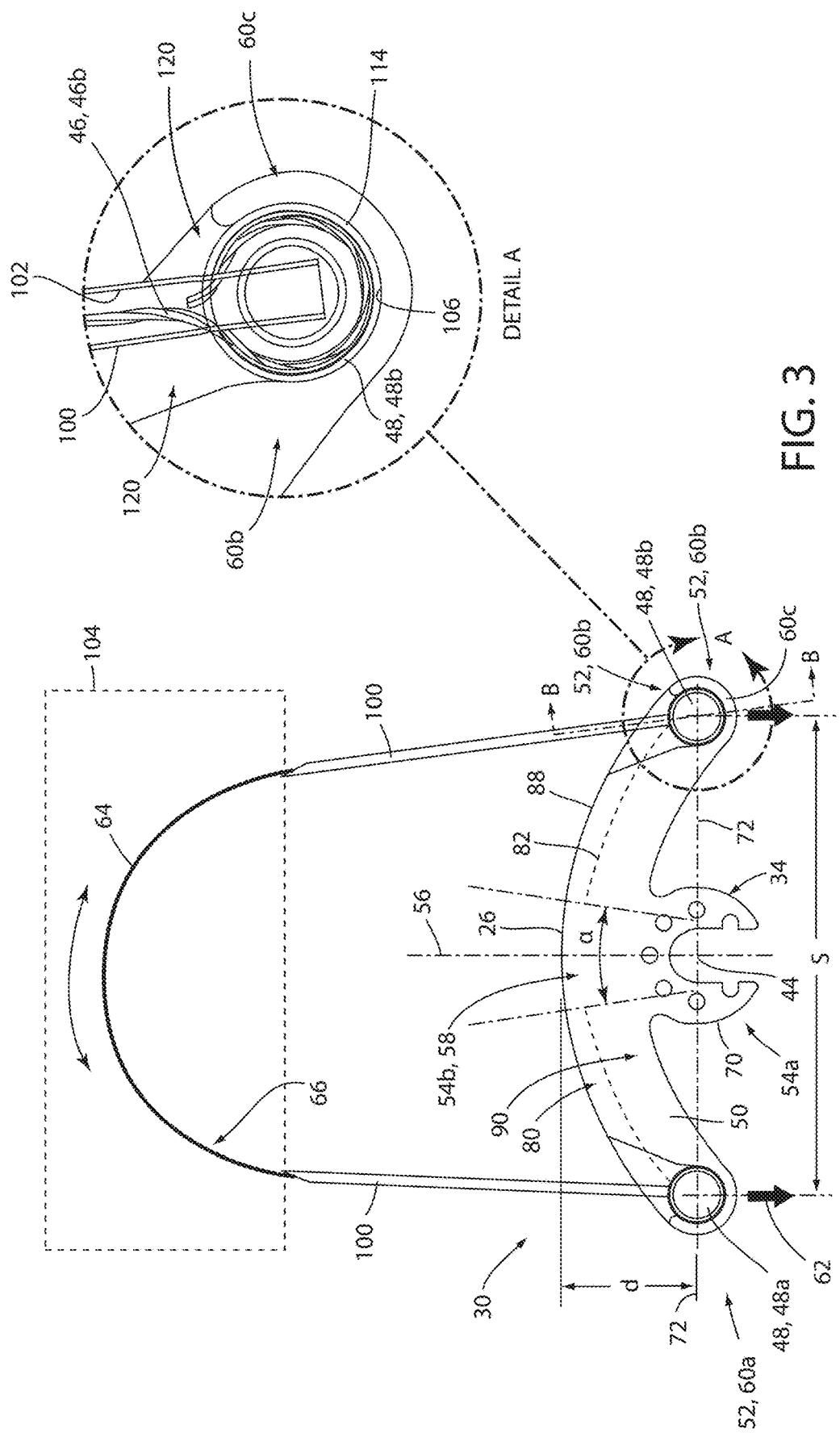
FIG. 3 is a top orthographic projected view of an adapter apparatus for a cable saw demonstrating a detailed view of a connection interface in Detail A.

Referring now to FIGS. 1-3, in various implementations, the lateral arms 50 may form opposing lateral wings in connection with the extension portion 58 and mirrored across the medial axis 56 of the adapter apparatus 30. The extension portion 58 may extend outward from the central axis 44 of the hub adapter 34 over a reach or extension distance d as shown in FIG. 3. In this configuration, the lateral arms 50 may extend perpendicularly outward from the extension portion 58 proximate to the distal end portion 54b, which may terminate at the extension distance d. Accordingly, in an assembled configuration wherein the hub adapter 34 is engaged by the mounting hub 24, the lateral arms 50 may extend outward from the medial axis 56 on the opposing sides 52 beyond or outside of a mouth 68 of the mounting hub 24. In addition to or contemporaneous to the lateral extension of the lateral arms 50, the first arm 50a and the second arm 50b may wrap partially around a perimeter 70 of the hub adapter 34 and extend back from the distal end portion 54b toward the proximal end portion 54a. For example, the lateral arms 50 may extend outward perpendicular from the medial axis 56 and curve back from the distal end portion 54b toward the proximal end portion 54a. In this configuration, the lateral end portions 60a, 60b may generally be laterally offset from or align with a lateral hub axis 72 that extends perpendicular to the medial axis 56 and passes through the central axis 44. In this way, the connecting features 48a, 48b may form the connection interface 48 on the opposing sides 52 and may be aligned with the lateral hub axis 72.

Referring to FIGS. 1, 2A, and 2B, the lateral arms 50 extending from the extension portion 58 of the adapter apparatus 30 may include a lateral support 80, support rib, or lateral reinforcement feature. The lateral support may improve the rigidity of the lateral arms 50, particularly in response to the rapid angular oscillations over the angular range α and the corresponding alternating tension 62 applied to the lateral end portions 60a, 60b. The lateral support 80 may extend from the distal end portion 54b along an oscillation path 82, which may be defined by a smooth radius of curvature 84 extending from the distal end portion 54b to the lateral end portions 60a, 60b. For example, the oscillation path 82 may extend from the intersection between the distal end portion 54b and the medial axis 56 to each of the connecting features 48a, 48b along a convex path extending back to the lateral hub axis 72. In this configuration, the lateral support 80 may be in connection with or form the extension portion 58 of the hub adapter 34. The hub adapter 34 may form a first thickness $T_1$ and the lateral support 80 may form a second thickness $T_2$ that is greater or thicker than the first thickness $T_1$. In this configuration, the lateral support 80 or support rib may provide for improved stability of the lateral arms 50 in cases where cantilevered loading is applied to the lateral end portions 60a, 60b to oppose the alternating tension 62 applied by the opposing wire ends 46 of the cable saw 32.

Referring to FIG. 2B, the first thickness $T_1$ may extend from the hub adapter 34 toward the extension portion 58 and outward to an intermediate lateral extent 86 of the lateral arms 50. Further, the second thickness $T_2$ of the lateral support 80 may extend along a distal perimeter edge 88 of the adapter apparatus 30 along the oscillation path 82. The second thickness $T_2$ of the lateral support 80 may continue from the distal perimeter edge 88 to the lateral end portions 60 forming the opposing sides 52 of the lateral arms 50 and may at least partially enclose a perimeter 60c of the lateral end portions 60a, 60b connecting features 48a, 48b. In this configuration, the improved strength and rigidity provided by the lateral support 80 may extend from the medial axis 56 of the extension portion 58 outward to the lateral end portions 60 over the span S to provide support for various forces that may be introduced as a result of the rapid oscillation and alternating tension 62 applied by the cutting wire 64 of the cable saw 32 to the adapter apparatus 30. Additionally, the first thickness $T_1$ may extend along a proximal portion of a bottom face 92 of the lateral arms 50 and form a recess 94 that extends from the medial axis 56 along the proximal end portion 90 of the arms 50 to the intermediate lateral extent 86.

Referring to FIGS. 1-3, the adapter apparatus 30 may further include one or more support guides 100, which may correspond to rigid or semi-rigid, tubular or pipe-like support structures. The support guides 100 may extend from the connection interface 48 and receive the opposing wire ends 46 of the cutting wire 64 within interior guide passages 102 formed by the support guides 100. The support guides 100 may extend along the opposing wire ends 46 from the connecting features 48a, 48b and in line with a cutting plane 104 of the cable saw 32 as shown in FIGS. 2A and 3. In this configuration, the cutting plane 104 may be oriented perpendicular to the rotational axis 42 of the drive head 12 and elevationally aligned with the hub adapter 34. The force applied to the hub adapter 34 via the mounting hub 24 of the oscillating drive head 12 may be communicated along the support guides 100 through the interior guide passages in alignment with the cutting plane 104. The resulting alternating tension 62 applied to the opposing wire ends 46 may be maintained in line with the cutting plane 104. Accordingly, the support guides 100 or tubular supports may provide for improved operation of the cable saw 32 by maintaining the directional alignment of the cutting wire 64 with the cutting plane 104 for improved cutting results and consistency.

Figure 4A:
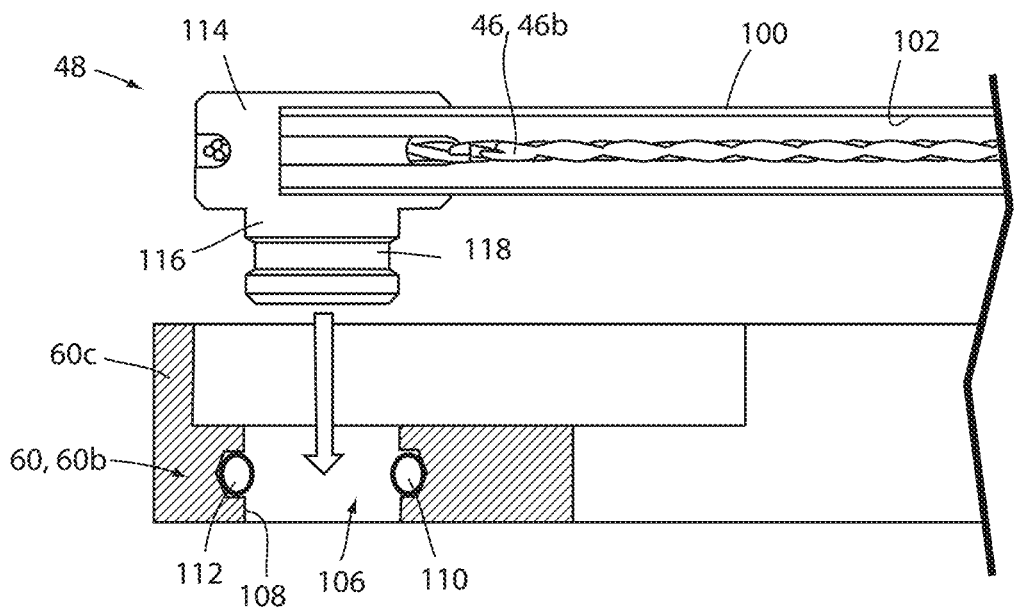
FIG. 4A is a detailed cross-sectional view along section line B-B demonstrated in FIG. 3 illustrating a connection interface of a cable saw adapter.
Figure 4B:
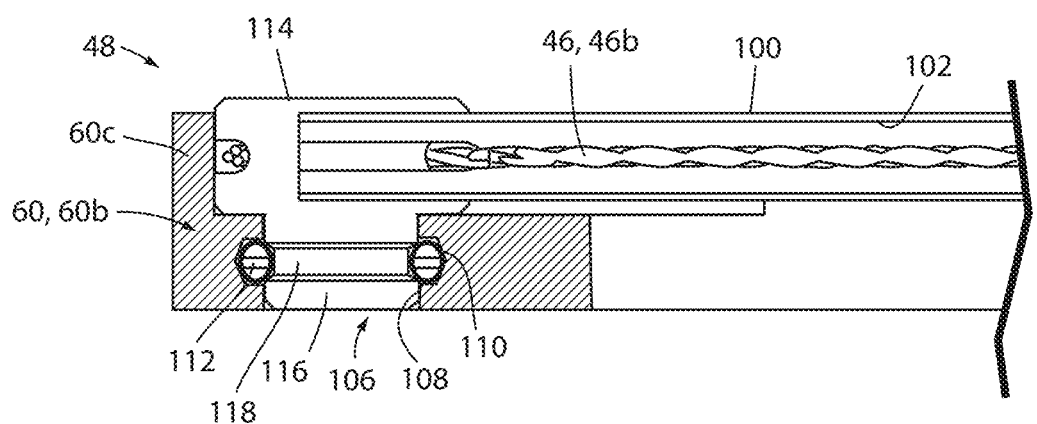
FIG. 4B is a detailed cross-sectional view along section line B-B demonstrated in FIG. 3 illustrating a connection interface of a cable saw adapter.

Referring now to FIGS. 3, 4A, and 4B, as previously discussed, the connection interface 48 may comprise a first connecting feature 48a disposed in or connected to the first lateral end portion 60a and a second connecting feature 48b disposed in or connected to the second lateral end portion 60b. In some implementations, one or more of the connecting features 48a, 48b forming the connection interface 48 may include a receiving aperture 106 formed in the lateral end portion 60 of the lateral arm 50. As demonstrated, each of the connecting features 48 may include the receiving aperture 106, which may be formed by a round or cylindrical interior wall 108 that extends through the lateral end portions 60. A receiving groove 110 may be formed in the interior wall 108 of the receiving aperture 106, which may be configured to receive a retaining spring 112. The retaining spring 112 may correspond to a round or toroidal retaining spring that conforms to the receiving groove 110, such that a portion of the retaining spring 112 is recessed within the cylindrical interior wall 108.

In order to mate the opposing wire ends 46 of the cable saw 32 to the receiving apertures 106, mounting pins 114 may be secured to each of the opposing wire ends 46 via a crimp, fastener, or other suitable means. In various embodiments, mounting pins 114 may form cylindrical mating protrusions 116 configured to engage the receiving apertures 106 in a clearance fit configuration. Each of the cylindrical mating protrusions 116 may further include a complementary engaging groove 118 that aligns with the receiving groove 110 when the cylindrical mating protrusion 116 is seated within the receiving aperture 106. In this configuration, the insertion and seating of the cylindrical mating protrusion 116 within the receiving aperture 106 may align the receiving groove 110 with the complementary engaging groove 118, such that the retaining spring 112 engages each of the grooves 110, 118 and retains the mounting pin 114 within the receiving aperture 106. In this way, the mounting pins 114 may detachably retain the opposing wire ends 46 in connection with the receiving apertures 106 forming the connection interface 48.

As shown in Detail A of FIG. 3, the engagement of the mounting pins 114 with the receiving apertures 106 may allow the mounting pins 114 to rotate within the receiving apertures 106. The rotation of the mounting pins 114 within the receiving apertures may allow the support guides 100 to sway or pivot about the connection interface 48 formed between the mounting pins 114 and the receiving apertures 106. In order to accommodate the swaying or pivoting, a clearance opening 120 or channel may be formed in the lateral end portions 60 on opposing sides of the cutting wire 64 of the cable saw 32 where the support guides 100 engage the connection interface 48. Accordingly, a sweeping path of the cable saw 32 and the support guides 100 that results from the alternating seesaw motion of the adapter apparatus 30 extends through the clearance opening 120. In this way, the swaying rotation of the cable saw 32 and the support guides 100 freely oscillates within the clearance opening 120 without interference from the lateral end portions 60 of the adapter apparatus 30.

Figure 5:
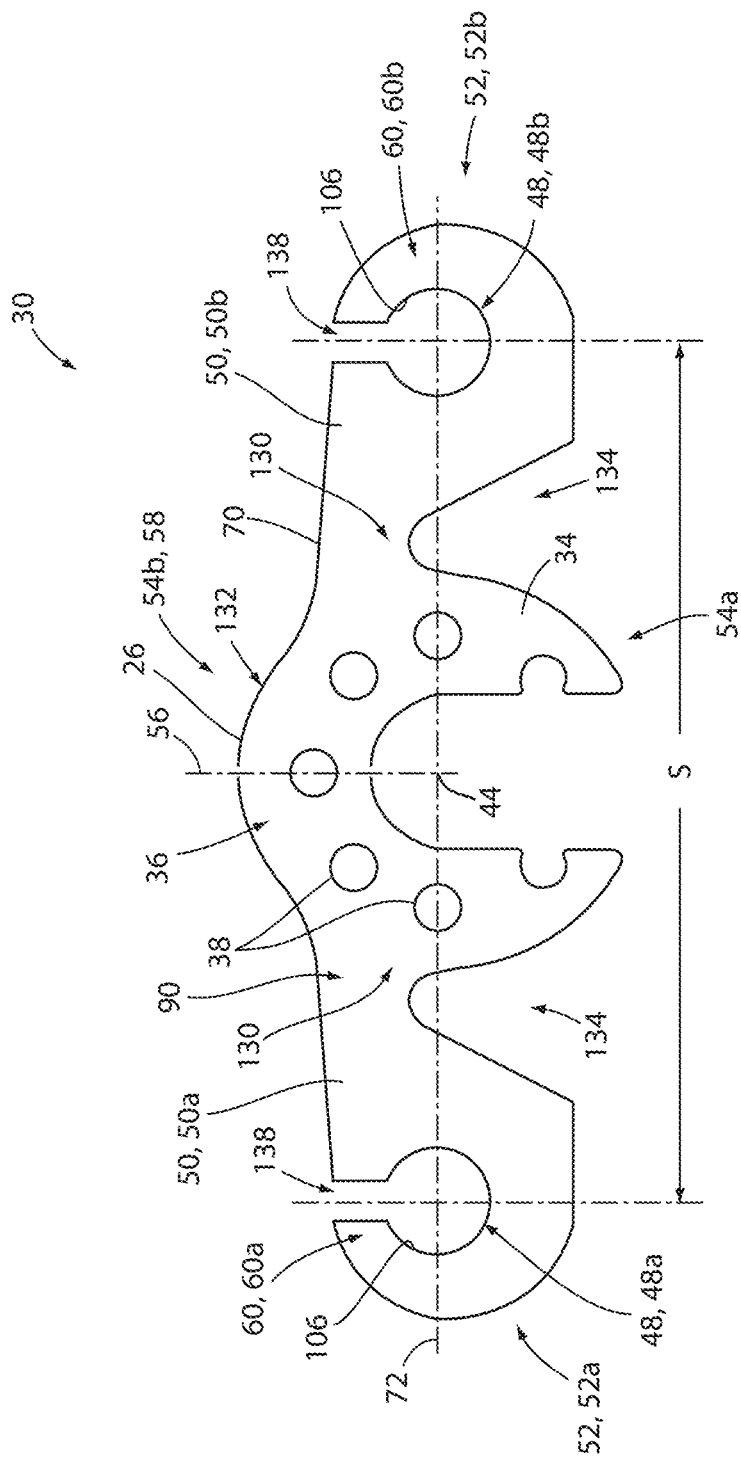
FIG. 5 is a top orthographic projected view of an adapter apparatus for a cable saw in accordance with the disclosure.

Referring now to FIG. 5, an exemplary embodiment of the adapter apparatus 30 is shown demonstrating the lateral arms 50 extending outward along the lateral hub axis 72 from the distal end portion 54b of the hub adapter 34. For example, rather than extending outward along the extension portion 58 as previously discussed in FIGS. 1-4, the lateral arms 50 may extend outward from an intermediate portion 130 of the hub adapter 34 near the distal end portion 54b. In such embodiments, the distal extent 26 of the adapter apparatus 30 may form a rounded protrusion 132 extending from the hub adapter 34. In this configuration, the hub adapter 34 may be inserted into the mouth 68 of the mounting hub 24 of the oscillating drive head 12 in an assembled configuration, and the lateral arms may extend outward from the mouth 68 along the distal end portion 54b. Accordingly, the adapter apparatus 30 may incorporate the lateral arms 50 extending outward along the lateral hub axis 72 from the hub adapter 34 to align the first connecting feature 48a and the second connecting feature 48b with the central axis 44 along the lateral hub axis 72.

As shown in FIG. 5, the top orthographic view of the adapter apparatus 30 may be implemented with a variable thickness (e.g., a first thickness $T_1$ and a second thickness $T_2$), similar to the implementations demonstrated in FIGS. 1-4 or, alternately, may include a consistent thickness extending from the hub adapter 34 outward along the lateral arms 50. In various implementations, the connection interface 48 may provide for the connecting features 48a, 48b to be positioned laterally outward along the span S between the lateral end portions 60a, 60b of the lateral arms 50. In this configuration, the opposing wire ends 46 of the cable saw 32 may be connected to the hub adapter 34, mirrored across the medial axis 56, and separated over the span S.

In some embodiments, each of the lateral arms 50 may extend outward from the hub adapter 34 and incorporate a cutout portion 134 extending from the proximal end portion 54a, toward the lateral hub axis 72, and outward along the lateral arms 50 to the opposing lateral end portions 60a, 60b. The cutout portion 134 may provide for the hub adapter 34 to be received within the mouth 68 of the mounting hub 24 to avoid interference between the lateral arms 50 and the mounting hub 24. Finally, the connecting features 48a, 48b forming the connection interface 48 with the cable saw 32 may correspond to the receiving apertures 106 with mounting openings 138 extending from the receiving apertures 106 outward to the distal perimeter edge 88 of each of the lateral arms 50. In this configuration, the mounting openings 138 may provide for the receiving apertures 106 to flex in order to receive the mounting pins 114 of the cable saw 32. Though the specific features and properties of the adapter apparatus 30 are discussed separately in reference to the embodiments of FIGS. 1-4 and 5, each of the features may be incorporated in various combinations without departing from the spirit of the disclosure.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents.

What is claimed:

1. An adapter apparatus for a cable saw comprising:
   a hub adapter that extends along a length from a proximal end portion to a distal end portion and detachably engages a mounting hub of an oscillating power tool; and
   a pair of lateral arms extending laterally outward on opposing sides of the hub adapter and extending proximally along the length toward a lateral hub axis of the mounting hub to a connection interface of the cable saw, wherein the connection interface is laterally offset from the mounting hub over a span and longitudinally positioned proximal of the distal end portion of the hub adapter.

2. The adapter apparatus according to claim 1, wherein the mounting hub defines a rotational axis of a drive shaft of the oscillating power tool and the rotational axis extends centrally through the hub adapter in an assembled configuration.

3. The adapter apparatus according to claim 1, wherein the hub adapter comprises a plurality of openings forming a mounting pattern that engages a mounting assembly of the mounting hub.

4. The adapter apparatus according to claim 1, wherein the distal end portion of the hub adapter forms an extension portion distal of the mounting hub, and wherein a distal extent of the lateral arms is positioned laterally from the hub adapter between the proximal end portion and the distal end portion.

5. The adapter apparatus according to claim 4, wherein the lateral arms form lateral wings mirrored across a medial axis extending from the proximal end portion of the hub adapter through a distal end portion of the extension portion, wherein each of the lateral arms extend from the extension portion to lateral end portions.

6. The adapter apparatus according to claim 5, wherein the lateral arms comprise a first arm and a second arm opposite the first arm, and the extension portion extends to an extension distance along a medial axis of the adapter apparatus from the hub adapter.

7. The adapter apparatus according to claim 6, wherein the first arm and the second arm extend laterally outward from the distal end portion of the extension portion and wrap partially around a perimeter of the hub adapter from the extension portion to the span.

8. An adapter apparatus for a cable saw comprising:
   a hub adapter that detachably engages a mounting hub of a power tool;
   an extension portion in connection with the hub adapter, wherein the hub adapter forms a proximal end portion of the adapter apparatus and extends outward to a distal end portion formed by the extension portion;
   a first lateral arm and a second lateral arm extending laterally outward from the extension portion on opposing sides to a first lateral end portion and a second lateral end portion;
   a connection interface comprising a first connecting feature and a second connecting feature laterally offset over a span, wherein the first connecting feature is formed in the first lateral end portion and the second connecting feature is formed in the second lateral end portion, and wherein the connection interface connects to wire ends of a cutting wire of the cable saw; and
   a support guide extending around a cable of the cable saw from the connection interface to a distal guide extent proximate to a cutting segment of the cable saw.

9. The adapter apparatus according to claim 8, wherein the extension portion forms a medial distal extent of the adapter apparatus extending outward along a medial axis from the hub adapter.

10. The adapter apparatus according to claim 8, wherein the first connecting feature and the second connecting feature of the connection interface are laterally aligned with a rotational axis of the hub adapter.

11. The adapter apparatus according to claim 10, wherein the mounting hub is in connection with a driving head of the power tool, and the power tool generates an oscillating motion defining an arc-shaped stroke that rotates the adapter apparatus about the rotational axis.

12. The adapter assembly according to claim 11, wherein the support guide extends from the connection interface along a guide plane perpendicular to the rotational axis.

13. The adapter apparatus according to claim 11, wherein the oscillating motion of the arc-shaped stroke adjusts a circumferential position of the cutting segment of the cable saw along a guide plane.

14. The adapter apparatus according to claim 8, further comprising:
   a lateral support extending from the distal end portion along an oscillation path of the first lateral arm and the second lateral arm.

15. The adapter apparatus according to claim 14, wherein the lateral support forms a first thickness and the hub adapter forms a second thickness, wherein the second thickness is less than the first thickness.

16. An adapter apparatus for a cable saw comprising:
   a hub adapter that detachably engages a mounting hub of a power tool and extends from a proximal end portion to a distal end portion, wherein the hub adapter extends outward over an extension distance along a medial axis from the hub adapter to the distal end portion;
   a first lateral arm and a second lateral arm opposite the first lateral arm, the first lateral arm and the second lateral arm extending laterally outward from opposing sides of the hub adapter to lateral end portions; and
   a connection interface of the cable saw in connection with the lateral end portions of each of the first lateral arm and the second lateral arm, wherein the connection interface is laterally offset over a span between the lateral end portions of the first lateral arm and the second lateral arm, wherein the connection interface comprises at least one connection feature disposed on a first lateral end portion of the first lateral arm or a second lateral end portion of the second lateral arm, wherein the at least one connection feature comprises a receiving aperture comprising a groove in which a retaining spring is disposed.

17. The adapter apparatus according to claim 16, wherein the cable saw comprises at least one mounting pin in connection with a wire end of a cutting wire, wherein the mounting pin engages the receiving aperture and is free to rotate within the receiving aperture.

18. The adapter apparatus according to claim 16, wherein the receiving aperture forms an interior wall defining an inner diameter, and the groove is formed in the interior wall of the receiving aperture.

19. An adapter apparatus for a cable saw comprising:
- a hub adapter that detachably engages a mounting hub of a power tool, wherein the hub adapter extends longitudinally from a proximal end portion in connection with the mounting hub to a distal end portion;
- a first lateral arm and a second lateral arm extending laterally outward from opposing sides of the hub adapter to a first lateral end portion and a second lateral end portion; and
- a connection interface comprising a first connecting feature and a second connecting feature laterally offset over a span, wherein the first connecting feature is formed in the first lateral end portion and the second connecting feature is formed in the second lateral end portion, wherein the connection interface connects to a saw apparatus, and wherein the first connecting feature and the second connecting feature of the connection interface are longitudinally positioned on the first lateral arm and the second lateral arm laterally along a length of the mounting hub.

20. The adapter apparatus according to claim 19, wherein the length of the mounting hub extends between a proximal hub end and a distal hub end of the mounting hub.

21. The adapter apparatus according to claim 19, wherein the first connecting feature and the second connecting feature of the connection interface are laterally aligned with a rotational axis of the hub adapter.

* * * * *